United States Patent
Ju et al.

(10) Patent No.: US 10,344,304 B2
(45) Date of Patent: Jul. 9, 2019

(54) MATERIALS DERIVED FROM FERMENTATION-PRODUCED RHAMNOLIPIDS AND METHODS OF PRODUCTION

(71) Applicants: Lu-Kwang Ju, Akron, OH (US); Shida Miao, Washington, DC (US)

(72) Inventors: Lu-Kwang Ju, Akron, OH (US); Shida Miao, Washington, DC (US)

(73) Assignee: THE UNIVERSITY OF AKRON, Akron, OH (US)

( * ) Notice: Subject to any disclaimer, the term of this patent is extended or adjusted under 35 U.S.C. 154(b) by 47 days.

(21) Appl. No.: 15/127,172

(22) PCT Filed: Mar. 19, 2015

(86) PCT No.: PCT/US2015/021488
§ 371 (c)(1),
(2) Date: Sep. 19, 2016

(87) PCT Pub. No.: WO2015/143169
PCT Pub. Date: Sep. 24, 2015

(65) Prior Publication Data
US 2017/0175151 A1    Jun. 22, 2017

Related U.S. Application Data

(60) Provisional application No. 61/955,849, filed on Mar. 20, 2014.

(51) Int. Cl.
| | | |
|---|---|---|
| *C11C 1/02* | (2006.01) |
| *C12P 7/64* | (2006.01) |
| *C07H 13/04* | (2006.01) |
| *C07H 13/06* | (2006.01) |
| *C08G 18/42* | (2006.01) |
| *C08G 18/73* | (2006.01) |
| *C12P 19/44* | (2006.01) |

(52) U.S. Cl.
CPC ............ *C12P 7/6409* (2013.01); *C07H 13/04* (2013.01); *C07H 13/06* (2013.01); *C08G 18/4263* (2013.01); *C08G 18/73* (2013.01); *C11C 1/025* (2013.01); *C12P 7/64* (2013.01); *C12P 19/44* (2013.01)

(58) Field of Classification Search
CPC .......... C12P 7/6409; C12P 19/44; C12P 7/64; C08G 18/73; C08G 18/4263; C11C 1/025; C07H 13/06; C07H 13/04
See application file for complete search history.

(56) References Cited

U.S. PATENT DOCUMENTS

| | | |
|---|---|---|
| 5,455,232 A | 10/1995 | Piljac et al. |
| 2004/0201117 A1 | 10/2004 | Anderson |
| 2009/0008325 A1 | 1/2009 | Ju et al. |
| 2010/0249058 A1 | 9/2010 | Ito et al. |
| 2011/0306569 A1 | 12/2011 | Yin et al. |
| 2012/0148502 A1 | 6/2012 | Hecht et al. |
| 2013/0310330 A1 | 11/2013 | Leighton |

FOREIGN PATENT DOCUMENTS

| | | |
|---|---|---|
| GB | 806935 | 1/1959 |
| WO | 2014039940 A1 | 3/2014 |

OTHER PUBLICATIONS

Magario, OV et al. "Kinetic Analysis and Modeling of the Liquid-Liquid Conversion of Emulsified di-Rhamnolipids by Naringinase From Penicillium decumbens" Biotechnology and Bioengineering, Jan. 1, 2009, vol. 102, No. 1, pp. 9-19; abstract; figure 1; p. 12, paragraph (1); p. 13, paragraph (3).

Foley, Petal. "Derivation and synthesis of renewable surfactants" Chem. Soc. Rev., 2012, vol. 41, pp. 1499-1518; p. 1510, paragraph [3].

*Primary Examiner* — Rabon A Sergent

(57) ABSTRACT

A method of preparing a product derived from a rhamnolipid includes the steps of: providing a rhamnolipid, combining the rhamnolipid with a reagent, allowing the rhamnolipid and reagent to react to form a product derived from the rhamnolipid, and collecting the product derived from the rhamnolipid. An exemplary product is dimeric β-hydroxy fatty acid.

16 Claims, 13 Drawing Sheets

MATERIALS DERIVED FROM FERMENTATION-PRODUCED RHAMNOLIPIDS AND METHODS OF PRODUCTION

GOVERNMENT LICENSE RIGHTS

This invention was made with government support under award #2009-10001-05112 awarded by the US Department of Agriculture/Department of Energy for "Supercritical Methods for Biorefinery of Rubber-Bearing Guayule Biomass." The government has certain rights in the invention.

CROSS-REFERENCE TO RELATED APPLICATION

This application is a non-provisional of U.S. Patent Provisional Application Ser. No. 61/955,849, filed on Mar. 20, 2014, the contents of which are incorporated herein by reference.

FIELD OF THE INVENTION

The present invention generally relates to novel materials derived from rhamnolipids. The present invention further relates to methods of making materials derived from rhamnolipids.

BACKGROUND OF THE INVENTION

Rhamnolipids are natural glycolipids (hybrid molecules of a carbohydrate and a lipid) that can be produced by the fermentation of *Pseudomonas* species and other organisms. The natural rhamnolipids produced from such fermentation are useful biosurfactants having an array of potential applications. However, the fermentation product is generally a mixture of many compounds, some of which are more useful than others. Also, the fermentation products can have limited uses based on their chemical structures.

Rhamnolipids include a rhamnose group. In its natural form, rhamnose is present as an L-form sugar. Sugars have chirality that is generally named by the spatial configuration of its atoms, as either L-form or D-form. Rhamnose's natural occurrence as an L-form sugar is rarer, as most natural sugars are in the D-form. Commercially, rhamnose is isolated from oak bark, citrus peel, and other plants and is presently used in some anti-wrinkle creams. However, obtaining rhamnose from these plant materials is labor intensive because in these sources, rhamnose is a minor component that is bound to, and associated with, complex materials.

Thus, a need in the art exists for novel compounds made from rhamnolipids. Such compounds can serve as biosurfactants. A need in the art also exists for novel processes for obtaining materials derived from rhamnolipids.

SUMMARY OF THE INVENTION

A first embodiment of this invention provides a compound having the following formula:

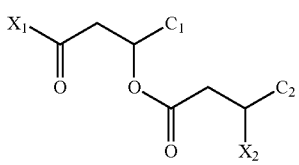

where C1 and C2 are each a hydrocarbon chain having between four and fourteen carbon atoms, and where X1 and X2 are each selected from the group consisting of a hydroxyl group and an alkoxy group.

A second embodiment provides a compound as in the first embodiment, wherein $C_1$ and $C_2$ are each alkyl chains having seven carbon atoms.

A third embodiment provides a compound as in either the first embodiment or the second embodiment, wherein $X_1$ and $X_2$ are each hydroxyl groups.

A fourth embodiment provides a polymer formed from a plurality of compounds from any of the foregoing embodiments.

A fifth embodiment provides a compound having the following formula:

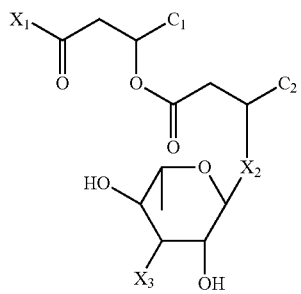

where C1 and C2 are each a hydrocarbon chain having between four and fourteen carbon atoms, where X1 is selected from the group consisting of a hydroxyl group and an alkoxy group, where X2 is oxygen, and where X3 is selected from the group consisting of

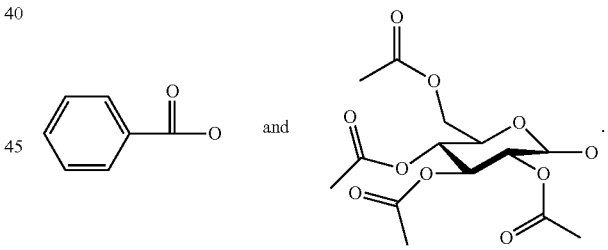

A sixth embodiment provides a compound as in the fifth embodiment, wherein $C_1$ and $C_2$ are each alkyl chains having seven carbon atoms.

A seventh embodiment provides a compound as in any of the fifth or sixth embodiments, wherein $X_3$ is

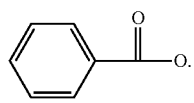

An eighth embodiment provides a compound as in and of the fifth through seventh embodiments, wherein $X_3$:

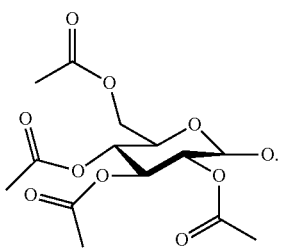

A ninth embodiment provides a polymer formed from a plurality of the compounds of the seventh embodiment.

A tenth embodiment provides a polymer formed from a plurality of the compounds of eighth embodiment.

An eleventh embodiment provides a method of preparing a product derived from a rhamnolipid comprising the steps of: providing a rhamnolipid, combining the rhamnolipid with a reagent, allowing the rhamnolipid and reagent to react to form a product derived from the rhamnolipid, and collecting the product derived from the rhamnolipid.

A twelfth embodiment provides a method as in the eleventh embodiment, wherein the reagent is an acid, wherein the reaction mixture further comprises an alcohol, wherein the rhamnolipid is a rhamnolipid mixture comprising both mono-rhamnolipids and di-rhamnolipids, and wherein the product is dimeric β-hydroxy fatty acid.

A thirteenth embodiment provides a method as in any of the eleventh through twelfth embodiments, wherein the rhamnolipid is a mono-rhamnolipid.

A fourteenth embodiment provides a method as in any of the eleventh through thirteenth embodiments further comprising the steps of: adding a catalyst to the collected product, and heating the collected product after the adding step, whereby the steps of adding and heating polymerize the dimeric β-hydroxy fatty acid.

A fifteenth embodiment provides a method as in any of the eleventh through fourteenth embodiments, wherein the reagent is a base in solution with an alcohol, wherein the rhamnolipid comprises two β-hydroxy fatty acids, and wherein the product is a rhamnolipid comprising only one β-hydroxy fatty acid.

A sixteenth embodiment provides a method as in any of the eleventh through fifteenth embodiments, wherein the reagent is an enzyme solution, wherein the rhamnolipid comprises two rhamnose residues, and wherein the product is a rhamnolipid comprising only one rhamnose residue.

A seventeenth embodiment provides a method as in any of the eleventh through sixteenth embodiments, wherein the reagent is benzoyl chloride.

An eighteenth embodiment provides a method as in any of the eleventh through seventeenth embodiments, wherein the reagent is acetylated glucose.

A nineteenth embodiment provides a method as in any of the eleventh through eighteenth embodiments, wherein the reagent is a diisocyanate, wherein the rhamnolipid is an ethylated rhamnolipid, and wherein the product is a polyurethane.

A twentieth embodiment provides a method as in any of the eleventh through nineteenth embodiments, wherein the reagent is a diisocyanate, wherein the rhamnolipid comprises a benzene attachment, and wherein the product is a polyurethane.

BRIEF DESCRIPTION OF THE DRAWINGS

Advantages of the present invention will become better understood with regard to the following description, appended claims, and accompanying drawings wherein:

DETAILED DESCRIPTION OF ILLUSTRATIVE EMBODIMENTS

Figure 1A:
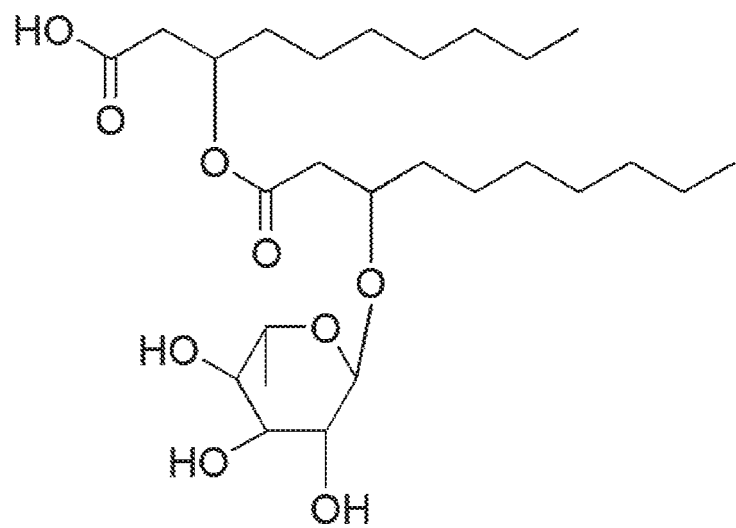
FIG. 1A is a schematic of a molecular structure of a mono-rhamnolipid comprising two β-hydroxy fatty acid chains and one rhamnose residue, where the β-hydroxy fatty acid chains each have ten carbons (R—$C_{10}$—$C_{10}$)

The present invention generally relates to novel biosurfactant materials. The present invention further relates to methods of making novel biosurfactant materials. The present invention further relates to novel biosurfactant materials derived from rhamnolipids.

Glycolipids are hybrid molecules of at least one carbohydrate and at least one lipid. Rhamnolipids (RLs) are a particular glycolipid produced by microorganisms. Rhamnolipids are commonly produced by the fermentation of Pseudomonas species. They act as biosurfactants and have antimicrobial activity against various bacteria and fungi.

Virtually any rhamnolipids may be employed in accordance with this invention. Rhamnolipids occur in two general categories, mono-rhamnolipids and di-rhamnolipids, where mono-rhamnolipids contain one rhamnose residue (hereinafter referred to as R) and di-rhamnolipids contain a chain of two rhamnose residues (hereinafter referred to as R—R).

In one or more embodiments, the one or more lipids of a rhamnolipid include six or more to twelve or less carbon atoms. In one or more embodiments, a rhamnolipid comprises two lipids, each being a hydroxyl fatty acid chain having from six to fourteen carbon atoms. In one or more embodiments, a rhamnolipid comprises one lipid, the lipid being a hydroxyl fatty acid chain having from six to fourteen carbon atoms. In one or more embodiments, a rhamnolipid comprises two lipids, each being a hydroxyl fatty acid chain having from eight to twelve carbon atoms. In one or more embodiments, a rhamnolipid comprises one lipid, the lipid being a hydroxyl fatty acid chain having from eight to twelve carbon atoms. In one or more embodiments, a rhamnolipid comprises two lipids, each being a hydroxyl fatty acid chain having ten carbon atoms. In one or more embodiments, a rhamnolipid comprises one lipid, the lipid being a hydroxyl fatty acid chain having ten carbon atoms. In one or more embodiments, a mixture of rhamnolipids comprises one or more of the above described rhamnolipids.

In one or more embodiments, rhamnolipids can have one or two molecules of rhamnose linked to a β-hydroxy fatty acid or one or two molecules of rhamnose linked to a chain of two β-hydroxy fatty acids joined by an ester bond. Two specific examples of rhamnolipids are rhamnosyl-β-hydroxydecanoyl-β-hydroxydecanoate (R—$C_{10}$—$C_{10}$), a mono-rhamnolipid; and rhamnosyl-rhamnosyl-β-hydroxydecanoyl-β-hydroxydecanoate (R—R—$C_{10}$—$C_{10}$), a di-rhamnolipid. These specific rhamnolipids are generally found in fermentation broths. Several homolog molecules with other fatty-acid chains, differing in chain length and/or the extent of saturation, have been identified as rhamnolipids. The rhamnolipids may generally be referred to as R—$C_n$, R—R—$C_n$, R—$C_n$—$C_m$, or R—R—$C_n$—$C_m$ where "n" and "m" indicate the number of carbons in each of the hydroxyl fatty acid chains. One or more of the hydroxyl fatty acid chains may also include one or more double bonds as to thereby become an alkene chain.

The present invention generally relates to the modification of rhamnolipids, including one or more processes of modification and one or more new compounds formed by the processes. The production of and providing of rhamnolipids is generally known to those skilled in the art. The details of the production processes are not critical to this invention, so long as the production process is suitable for providing rhamnolipids.

One such process of production is by way of fermentation methods. Fermentation is the process that utilizes microorganisms such as bacteria, yeast, and fungi to produce cell biomass and metabolic products. Fermentation methods are generally known to those skilled in the art. In one or more embodiments, rhamnolipids are produced by the fermentation of *Pseudomonas* species. A preferred *Pseudomonas* species is *Pseudomonas aeruginosa*, which produces a mixture of rhamnolipids having ten carbons as the predominant hydroxyl fatty acid chain length.

In one or more embodiments, the present invention generally relates to the modification of rhamnolipids and the new compounds thereby produced. Particular modification steps will be discussed in detail below, but generally can include one or more of the following steps: cleaving a glycosidic bond, hydrolyzing an ester bond, attaching a compound to a hydroxyl fatty acid residue, and attaching a compound to a rhamnose residue. One or more of compounds can result from one or more of the modification steps. One or more compounds can result from one or more additional steps of polymerization.

Figure 1B:
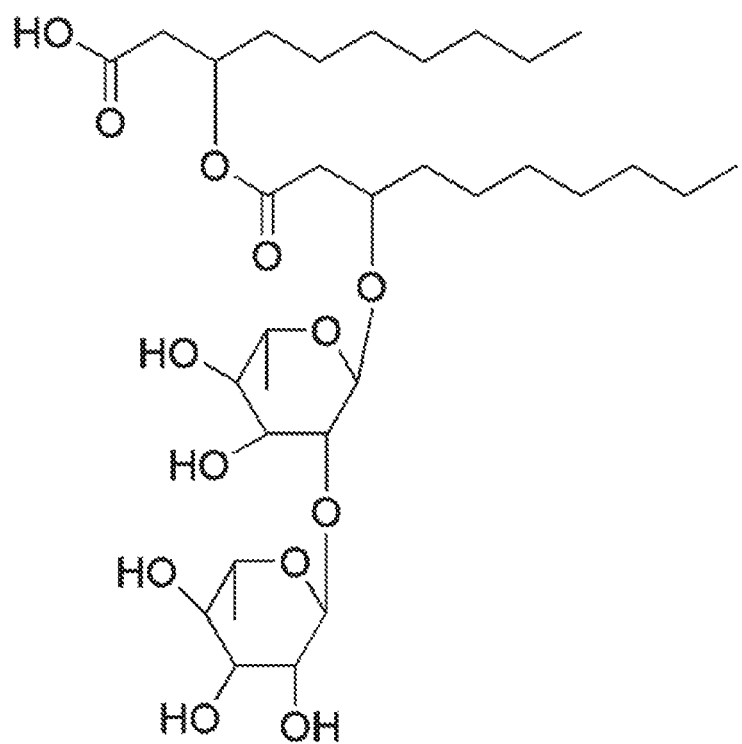
FIG. 1B is a schematic of a molecular structure of a di-rhamnolipid comprising two β-hydroxy fatty acid chains and a chain of two rhamnose residues, where the β-hydroxy fatty acid chains each have ten carbons (R—R—$C_{10}$—$C_{10}$)
Figure 2:
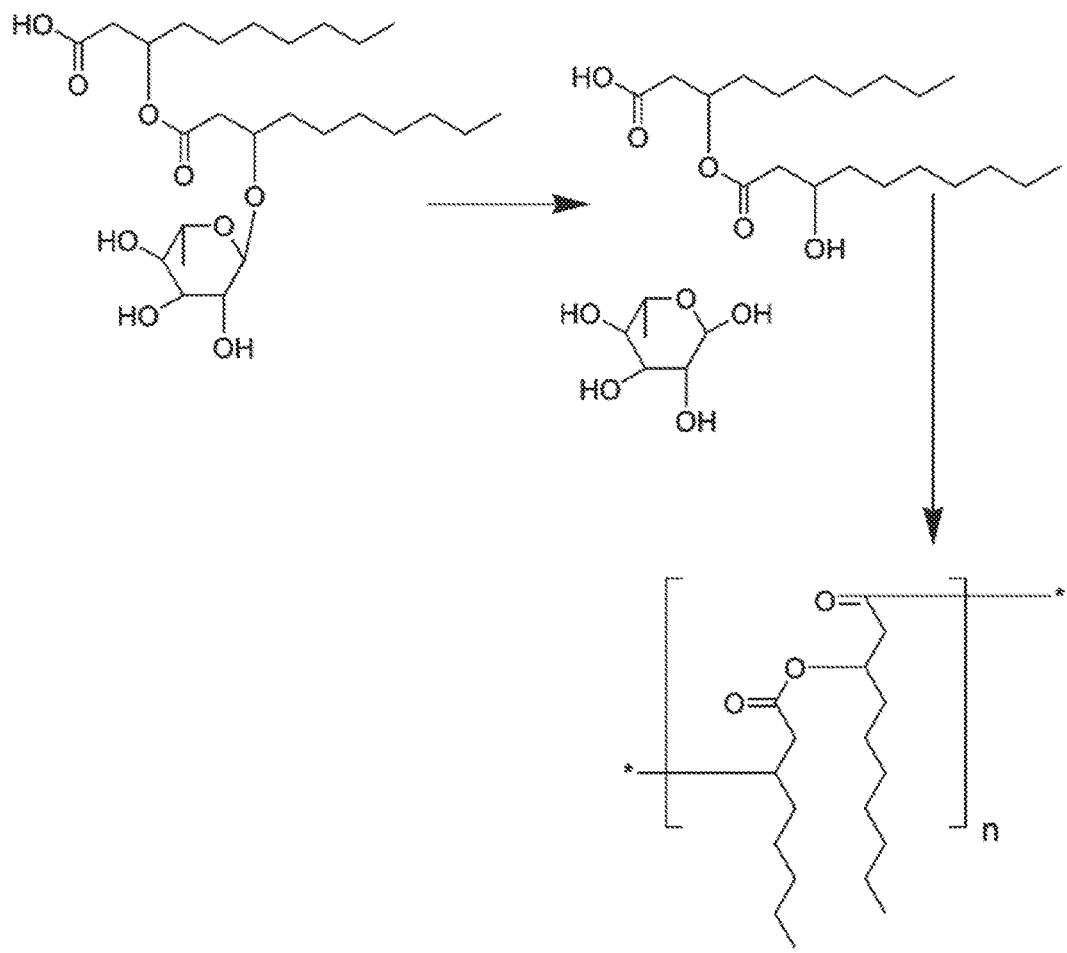
FIG. 2 is a schematic of a conversion of a mono-rhamnolipid (R—$C_{10}$—$C_{10}$) to the products of dimeric β-hydroxy fatty acid and rhamnose, and the subsequent polymerization of n units of dimeric β-hydroxy fatty acid.
Figure 4:
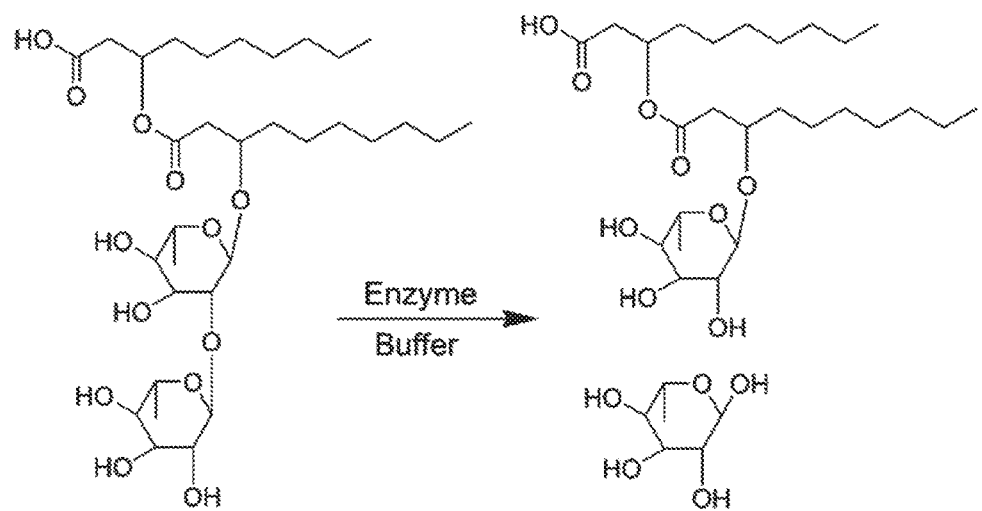
FIG. 4 is a schematic of a conversion of a di-rhamnolipid (R—R—$C_{10}$—$C_{10}$) to a mono-rhamnolipid (R—$C_{10}$—$C_{10}$) through the use of an enzyme and a buffer.

As shown in FIGS. 1 and 2, rhamnolipids can have an ester bond joining a chain of two β-hydroxy fatty acids and a glycosidic bond joining the rhamnose residue with one of the β-hydroxy fatty acids. As shown in FIG. 4, where two rhamnose residues are present, a glycosidic bond joins the two rhamnose residues. A glycosidic bond may be cleaved without breaking the ester bond between the two β-hydroxy fatty acids. The glycosidic bond joining two rhamnose residues may be cleaved without breaking the glycosidic bond joining the rhamnose residue with one of the β-hydroxy fatty acids and without breaking the ester bond between the two β-hydroxy fatty acids.

Where a rhamnolipid has the form R—R—$C_n$, R—R—$C_n$—$C_m$, R—$C_n$, or R—$C_n$—$C_m$, the rhamnose residue may be cleaved as to form the products of rhamnose and the lipid. Where a rhamnolipid has the form R—R—$C_n$—$C_m$ or R—$C_n$—$C_m$, the lipid product is $C_n$—$C_m$. The $C_n$—$C_m$ product can also be referred to as a $C_n$—$C_m$ compounds or a dimeric β-hydroxy fatty acid. The $C_n$—$C_m$ product can be represented by the formula

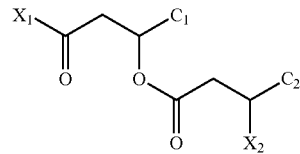

where $C_1$ and $C_2$ are each a hydrocarbon chain having between four and fourteen carbon atoms, and where $X_1$ and $X_2$ are each selected from the group consisting of a hydroxyl group and an alkoxy group. In one or more embodiments, $C_1$ and $C_2$ are each selected from the group consisting of an alkyl chain and an alkenyl chain. In one or more embodiments, $X_1$ and $X_2$ are each selected from the group consisting of an ethoxy group and a methoxy group. In one or more embodiments, $C_1$ and $C_2$ are each alkyl chains having seven carbon atoms, and $X_1$ and $X_2$ are each hydroxyl groups.

The forming of the $C_n$—$C_m$ product does not require activated monomers and special enzymes. The $C_n$—$C_m$ product has potential applications in the agricultural and medical fields, and can also be further polymerized in vitro via an easier synthetic route, which will be discussed later.

Advantageously, the $C_n$—$C_m$ product can be produced via extracellular metabolite rhamnolipids. Extracellular metabolites are excreted by the cells to the surrounding solution. Collecting extracellular metabolites does not require killing and re-growing the producing cells. Thus, the amount of extracellular products that can be produced is not limited by the volume of the cells themselves and higher volumetric productivity can be achieved.

One or more methods of performing a cleaving to form a $C_n$—$C_m$ product can include one or more of the following steps: combining rhamnolipids with an alcohol, where the rhamnolipids can be R—$C_n$—$C_m$, R—R—$C_n$—$C_m$, or a combination thereof, where the alcohol can be ethanol; adding an acid, where the acid can be sulfuric acid; reacting the resulting combination in a water bath, where the reaction can be for 4 h in a 70° C. water bath operating at 150 rpm; neutralizing the acid with a base, where the base can be a saturated aqueous solution of sodium bicarbonate; drying the neutralized sample; extracting the neutralized sample with a solvent, where the solvent can be ethyl acetate; collecting the solvent phase; drying the solvent phase; collecting the separated rhamnose product in a solid phase; reacting the solvent phase with a base to hydrolize ethyl diacids, where the base can be an aqueous sodium hydroxide solution, where the hydrolysis reaction can be performed for 2 h at 150 rpm and 25° C.; neutralizing the hydrolysis reaction product with an acid, where the acid can be acetic acid; drying the neutralized product; extracting the neutralized product with a solvent, where the solvent can be ethyl acetate; drying the solvent extract; and collecting free di-acids as a product. Said another way, a $C_n$—$C_m$ product can be formed by first forming an ethyl di-acid and then hydrolyzing to form a free di-acid.

A reaction solvent can be selected from the group consisting of methanol, ethanol, n-propanol, isopropyl alcohol, n-butanol, isobutyl alcohol, ethyl ether, ethylene glycol, 1,2-propandiol, 1,3-propandiol, 1,2-butyl glycol, 1,4-butyl glycol, and combinations thereof. A catalyst can be selected from the group consisting of sulfuric acid, hydrochloric acid, phosphoric acid, acetic acid, propionic acid lactic acid, and combinations thereof.

In one or more embodiments, the reaction temperature is in the range of from 30° C. or more to 90° C. or less. In one or more embodiments, the reaction temperature is in the range of from 60° C. or more to 80° C. or less.

In one or more embodiments, the reaction is first allowed to take place at a first predetermined temperature and then at a second predetermined temperature. In one or more embodiments, a first predetermined temperature is in the range of from 30° C. or more to 50° C. or less and a second predetermined temperature is in the range of from 50° C. or more to 90° C. or less.

In one or more embodiments, the reaction time is in a range of from 0.5 h or more to 7 h or less. In one or more embodiments, the time at a first predetermined temperature is in the range of from 0.5 h or more to 6.5 h or less and the time at a second predetermined temperature is in the range of from 0.5 h or more to 6.5 h or less.

Where a rhamnolipid has the form R—R—$C_n$, R—R—$C_n$—$C_m$, the second or outermost rhamnose residue may be cleaved as to form a mono-rhamnolipid from a di-rhamnolipid. A method of converting di-rhamnolipids, e.g. R—R—$C_n$ and R—R—$C_n$—$C_m$, to mono-rhamnolipids, e.g. R—$C_n$ and R—$C_n$—$C_m$, can be done in vitro.

Figure 3:
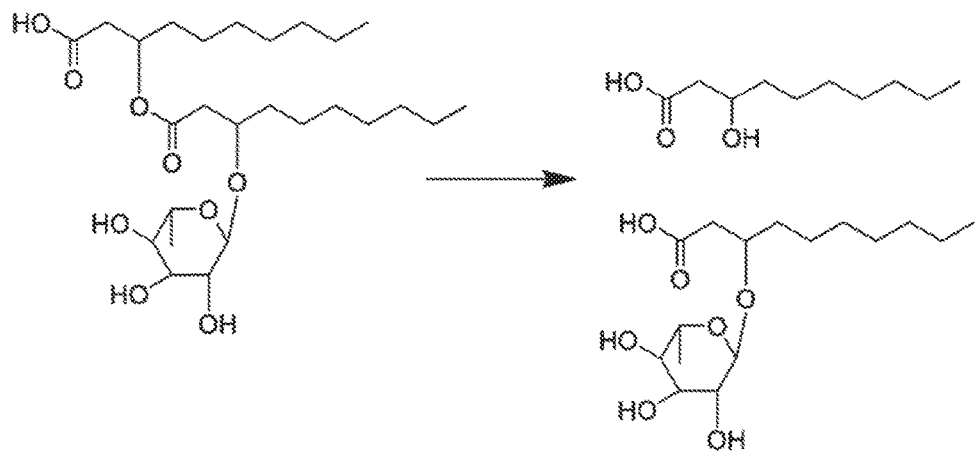
FIG. 3 is a schematic of a conversion of a mono-rhamnolipid (R—$C_{10}$—$C_{10}$) to the products of a β-hydroxy fatty acid and a rhamnolipid comprising one β-hydroxy fatty acid chain and one rhamnose residue (R—$C_{10}$)

A method for converting di-rhamnolipids to mono-rhamnolipids in vitro can include using an enzymatic reaction to selectively cleave the glycosidic bond between two rhamnose residues, without breaking the glycosidic bond joining the rhamnose residue with one of the β-hydroxy fatty acids, and without breaking the ester bond between the two β-hydroxy fatty acids. In this process, the enzymes break the glycosidic bond between the rhamnose residues, but they do not break the glycosidic bond between the β-hydroxy fatty acid residue and the rhamnose residue (i.e., R—Cn), presumably due to the stearic hindrance effect (FIG. 3).

Enzymatic reaction are known to those skilled in the art and include an enzyme having an active site being is shaped to accommodate the specific structure of the reactant, i.e. the substrate to the enzyme, or the part of the reactant where the reaction is to occur. In addition, the active site can have functional groups and properties to enable the desired reaction to happen. Thus, enzyme has an affinity to bind a specific reactant or similar structures and to catalyze a specific reaction. Suitable enzymes include those known to hydrolyze the bonds between sugar residues.

An enzyme can be selected from the group consisting of cellobiase, cellulase, xylanase, hemicellulase, pectinase, α-galactosidase, β-glucosidase, carbohydrase, and combinations thereof. A reaction solvent can be selected from the group consisting of citrate buffer, phosphate buffer, toluene, ethyl acetate, and combinations thereof.

In one or more embodiments, the reaction temperature is in the range of from 0° C. or more to 60° C. or less. In one or more embodiments, the reaction temperature is in the range of from 37° C. or more to 50° C. or less.

In one or more embodiments, the reaction is first allowed to take place at a first predetermined temperature and then at a second predetermined temperature. In one or more embodiments, a first predetermined temperature is in the range of from 0° C. or more to 37° C. or less and a second predetermined temperature is in the range of from 37° C. or more to 60° C. or less.

In one or more embodiments, the reaction time is in a range of from 0.5 h or more to 96 h or less. In one or more embodiments, the time at a first predetermined temperature is in the range of from 24 h or more to 72 h or less and the time at a second predetermined temperature is in the range of from 24 h or more to 72 h or less.

It is previously known that bacteria use the enzyme rhamnosyltransferase to make di-rhamnolipids in vivo. Because the ratio of mono-rhamnolipids to di-rhamnolipids in a produced rhamnolipid mixture can significantly affect the properties and effectiveness of the mixture, it is desirable to provide an improved method for adjusting this ratio. Following a conversion of di-rhamnolipids to mono-rhamnolipids in vitro as set forth herein, a mixture of rhamnolipids will have an adjusted ratio of mono-rhamnolipids to di-rhamnolipids.

The ratio of mono-rhamnolipids to di-rhamnolipids can be adjusted to any desired ratio. In one or more embodiments, a mixture of rhamnolipids has mono-rhamnolipids in a range of from 30% or more to 60% or less and di-rhamnolipids in a range of from 40% or more to 70% or less. In one or more embodiments, a mixture of rhamnolipids has mono-rhamnolipids in a range of from 50% or more to 60% or less and di-rhamnolipids in a range of from 40% or more to 50% or less. In one or more embodiments, a mixture of rhamnolipids has 55% mono-rhamnolipids and 45% di-rhamnolipids. In one or more embodiments, a composition of pure mono-rhamnolipids can be produced.

In one or more embodiments, a mixture having mono-rhamnolipids in a range of from 30% or more to 50% or less is converted to a mixture having mono-rhamnolipids in a range of from 50% or more to 60% or less. In one or more embodiments, a mixture having 40% mono-rhamnolipids is converted to a mixture having 55% mono-rhamnolipids.

In one or more embodiments, a mixture having di-rhamnolipids in a range of from 50% or more to 70% or less is converted to a mixture having di-rhamnolipids in a range of from 40% or more to 50% or less. In one or more embodiments, a mixture having 60% di-rhamnolipids is converted to a mixture having 45% di-rhamnolipids.

Where a rhamnolipid has the form R—$C_n$—$C_m$, R—R—$C_n$—$C_m$, the second or outermost β-hydroxy fatty acid residue may be selectively hydrolyzed while the glycosidic bond between the first β-hydroxy fatty acid residue and rhamnose is preserved. The ester bond between the two β-hydroxy fatty acid residues is selectively hydrolyzed, resulting in a product having only one β-hydroxy fatty acid residue, i.e. either R—$C_n$ or R—R—$C_n$. These products are generally not present in a fermentation-produced rhamnolipid mixture, or are present in only a very small amount.

One or more methods of performing a hydrolysis can include one or more of the following steps: providing rhamnolipids, where the rhamnolipids can be mono-rhamnolipids, di-rhamnolipids, or a combination thereof; combining rhamnolipids with a base solution, where the base solution can be sodium hydroxide in water or sodium methoxide in methanol; reacting the combined mixture, where the reaction can be for from 4 h to 6 h at 600 rpm and 50° C.; neutralizing the combined mixture with an acid, where the acid can be hydrochloric acid; removing a salt by centrifugation; removing a solvent by airflow; and collecting a product.

A reaction solvent can be selected from the group consisting of water, methanol, ethanol, n-propanol, isopropyl alcohol, ethyl ether, acetone, ethylene glycol, 1,2-propandiol, 1,3-propandiol, tetrahydrofuran, and combinations thereof. A catalyst can be selected from the group consisting of sodium hydroxide, potassium hydroxide, sodium methoxide, potassium methoxide, and combinations thereof.

In one or more embodiments, the reaction temperature is in the range of from 0° C. or more to 70° C. or less. In one or more embodiments, the reaction temperature is in the range of from 0° C. or more to 25° C. or less.

In one or more embodiments, the reaction is first allowed to take place at a first predetermined temperature and then at a second predetermined temperature. In one or more embodiments, a first predetermined temperature is in the range of from 0° C. or more to 30° C. or less and a second predetermined temperature is in the range of from 20° C. or more to 70° C. or less.

In one or more embodiments, the reaction time is in a range of from 0.5 h or more to 6 h or less. In one or more embodiments, the time at a first predetermined temperature is in the range of from 0.5 h or more to 4 h or less and the time at a second predetermined temperature is in the range of from 0.5 h or more to 4 h or less.

For any provided rhamnolipid, an additional modification step can include the attachment of a carbohydrate or a non-carbohydrate to a rhamnose residue. An attachment can also be added to the free carboxyl group of a rhamnolipid. The attachments can extend or improve the performance and potential uses of the rhamnolipid.

Rhamnolipids have a free carboxyl group which can make their properties pH-dependent. One example of an attachment is an attachment to this free carboxyl group. By attaching a group, such as a methyl or ethyl group, to the carboxyl group, which can be said to protect the carboxyl group, the obtained methylated or ethylated rhamnolipids can be used as nonionic surfactants.

One or more methods of attaching to a free carboxyl group of a rhamnolipid can include one or more of the following steps: providing rhamnolipids, where the rhamnolipids can be mono-rhamnolipids, di-rhamnolipids, or a combination thereof; combining rhamnolipids with an acid and an alcohol, where the acid can be sulfuric acid and the alcohol can be selected from the group consisting of ethanol and methanol; reacting the combination where the reaction can be for 24 h at 300 rpm and 0° C.; neutralizing the acid with a base, where the base can sodium methoxide in methanol; removing salt by centrifugation; collecting a supernatant; drying the supernatant under airflow to remove a solvent; dissolving a precipitate in a solvent to remove any salt remaining from the centrifugation, where the solvent can be toluene; removing the additional solvent by airflow; and collecting a product.

By introducing an additional chemical attachment to a rhamnose residue of a rhamnolipid, the properties of the resulting rhamnolipid can be further adjusted. An attachment to a rhamnose residue can also be done for a methylated or ethylated rhamnolipid.

An additional chemical attachment can be attached to a rhamnolipid having the general form of R—R—$C_n$—$C_m$ or R—$C_n$—$C_m$. A rhamnolipid of R—$C_n$—$C_m$ can be represented by the formula

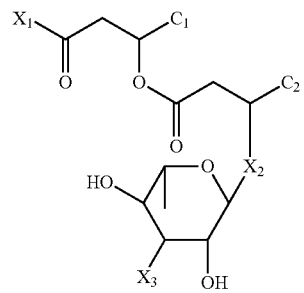

where $C_1$ and $C_2$ are each a hydrocarbon chain having between four and fourteen carbon atoms, where $X_1$ is selected from the group consisting of a hydroxyl group and an alkoxy group, where $X_2$ is oxygen, and where $X_3$ is defined as below. In one or more embodiments, $C_1$ and $C_2$ are each selected from the group consisting of an alkyl chain and an alkenyl chain. In one or more embodiments, $X_1$ is selected from the group consisting of an ethoxy group and a methoxy group. In one or more embodiments, $C_1$ and $C_2$ are each alkyl chains having seven carbon atoms, $X_1$ is a hydroxyl group, and $X_2$ is oxygen.

Figure 5:
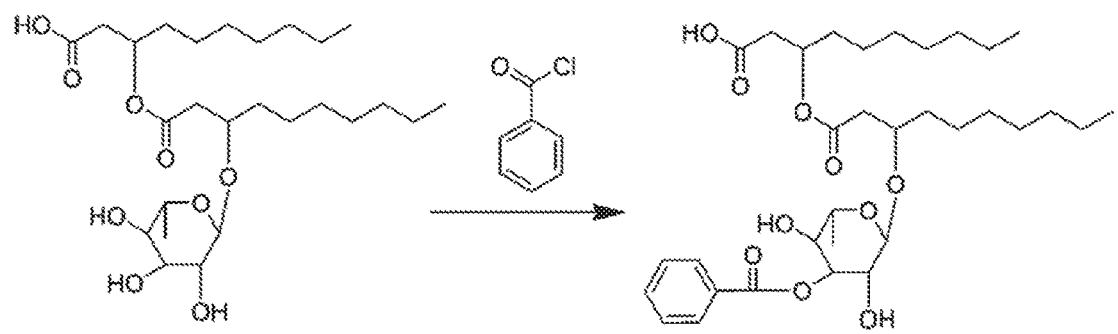
FIG. 5 is a schematic of a modification of a mono-rhamnolipid.
Figure 6:
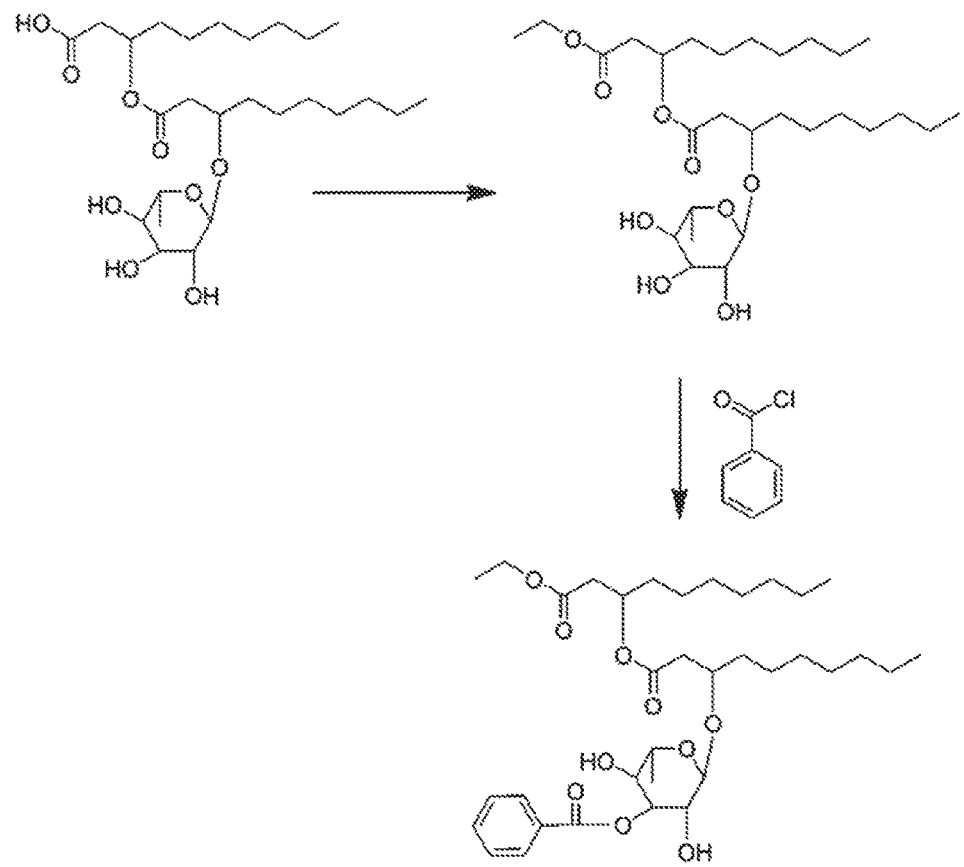
FIG. 6 is a schematic of a modification of a mono-rhamnolipid.

Suitable attachments can be non-carbohydrates, such as an attachment having a benzene ring as shown in FIGS. 5 and 6. In one or more embodiments, benzoyl chloride is used to attach a benzene ring to a rhamnolipid.

One or more methods of attaching to a rhamnose residue can include one or more of the following steps: providing rhamnolipids, where the rhamnolipids can be mono-rhamnolipids, di-rhamnolipids, or a combination thereof; combining rhamnolipids with an organochlorine compound, where the organochlorine compound can be benzoyl chloride; combining an organic nitrile with a tertiary amine, where the organic nitrile can be acetonitrile and the tertiary amine can be triethylamine; mixing the rhamnolipid combination with the organic nitrile combination on a droplet basis; reacting the combined mixture; and collecting a product.

An example of an $X_3$ for the above compound that is a non-carbohydrate is the compound

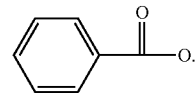

Figure 7:
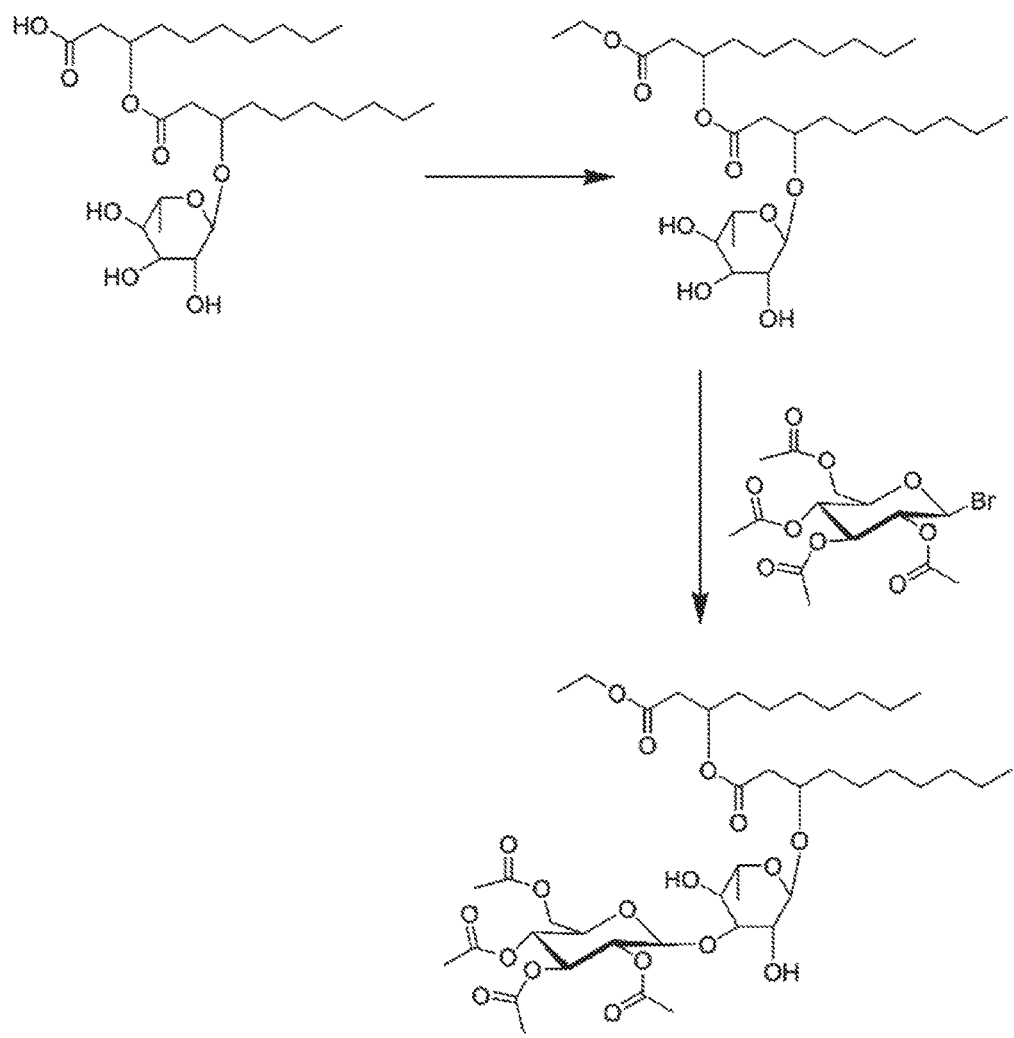
FIG. 7 is a schematic of a modification of a mono-rhamnolipid.

Suitable attachments can also be carbohydrates, such as acetylated glucose as shown in FIG. 7. The acetylated glucose can have varying extents of acetylation. In one or more embodiments, 2,3,4,6-tetra-β-D-glucopyranosyl is used to attach acetylated glucose to a rhamnolipid.

One or more methods of attaching to a rhamnose residue can include one or more of the following steps: providing rhamnolipids, where the rhamnolipids can be ethylated rhamnolipids, methylated rhamnolipids, or a combination thereof combining rhamnolipids with a reagent, where the reagent can be 2,3,4,6-tetra-β-D-glucopyranosyl bromide solution; adding an organic compound and a catalyst, where the organic compound can be 1,1,3,3-tetramethylurea and the catalyst can be silver carbonate; reacting the combined mixture while avoiding ambient light from contacting the combined mixture; and collecting a product.

An example of an $X_3$ for the above compound that is a carbohydrate is the compound

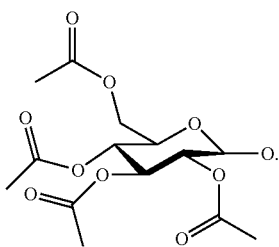

For both the carbohydrate and non-carbohydrate attachment reactions, a solvent can be selected from the group consisting of dichloromethane, trichloromethane, toluene, benzene, acetone, ethyl acetate, carbon tetrachloride, 1,4-dioxane, and combinations thereof. A reaction solvent can be selected from the group consisting of dichloromethane, trichloromethane, toluene, benzene, acetone, ethyl acetate, carbon tetrachloride, 1,4-dioxane, and combinations thereof. An acid absorber can be selected from the group consisting of triethylamine, pyridine, and 1,1,3,3-tetramethylurea. For carboxyl protected rhamnolipids, 2,3,4,6-tetra-β-D-glucopyranosyl bromide can be used to react with the rhamnolipid. A catalyst can be a silver salt, such as silver carbonate and silver trifluoromethanesulfonate.

In one or more embodiments, the reaction temperature is in the range of from −70° C. or more to 50° C. or less. In one or more embodiments, the reaction temperature is in the range of from 0° C. or more to 25° C. or less.

In one or more embodiments, the reaction is first allowed to take place at a first predetermined temperature and then at a second predetermined temperature. In one or more embodiments, a first predetermined temperature is in the range of from −70° C. or more to 0° C. or less and a second predetermined temperature is in the range of from −25° C. or more to 50° C. or less.

In one or more embodiments, the reaction time is in a range of from 0.5 h or more to 8 h or less. In one or more embodiments, the time at a first predetermined temperature is in the range of from 0.5 h or more to 7.5 h or less and the time at a second predetermined temperature is in the range of from 0.5 h or more to 7.5 h or less.

One or more methods of the present invention can include a step of polymerization. One or more compounds of the present invention are polymers formed by such steps of polymerization. Polymerization can be done with a $C_n$—$C_m$ product and with modified rhamnolipids.

The above described dimeric β-hydroxy fatty acids can be a natural feedstock to form polyesters and co-polyesters. This polymerization is shown in FIG. 2. The pendant alkyl and/or alkenyl chains add a unique feature to the obtained polymers. The resulting polyhydroxyalkanoates or polyhydroxyalkenoates (PHAs) can be used as biodegradable bioplastics.

The polymerization can be conducted with or without solvent. Suitable solvents can be selected from the group consisting of dichloromethane, trichloromethane, toluene, benzene, acetone, ethyl acetate, carbon tetrachloride, 1,4-dioxane, and combinations thereof. Suitable catalysts can be selected from the group consisting of titanium(IV) ethoxide, titanium(IV) isopropoxide, titanium(IV) butoxide, dibutyl-tin dilaurate, tin(II) octanoate, and combinations thereof.

The dimeric β-hydroxy fatty acid building block can also be copolymerized with other reactive chemicals into various copolymers. Suitable copolymers can be selected from the group consisting of lactic acid, lactide, 3-hydroxypropionic acid, 4-hydroxybutyric acid, 10-hydroxydecanoic acid, 16-hydroxyhexadecanoic acid, and combinations thereof.

In one or more embodiments, the reaction temperature is in the range of from 25° C. or more to 210° C. or less. In one or more embodiments, the reaction temperature is in the range of from 150° C. or more to 200° C. or less.

In one or more embodiments, the reaction is first allowed to take place at a first predetermined temperature and then at a second predetermined temperature. In one or more embodiments, a first predetermined temperature is in the range of from 25° C. or more to 150° C. or less and a second predetermined temperature is in the range of from 150° C. or more to 200° C. or less.

In one or more embodiments, the reaction time is in a range of from 0.5 h or more to 5 h or less. In one or more embodiments, the time at a first predetermined temperature is in the range of from 0.5 h or more to 4 h or less and the time at a second predetermined temperature is in the range of from 0.5 h or more to 4 h or less.

A variety of additional polymeric materials can be made with the dimeric β-hydroxy fatty acid building block using methods and chemicals known to those skilled in the art.

One or more methods of polymerization using a $C_n$—$C_m$ product can include one or more of the following steps: providing a $C_n$—$C_m$ product, where the $C_n$—$C_m$ product can be a dimeric β-hydroxy fatty acid; purging with nitrogen; adding a catalyst, where the catalyst can be titanium(IV) butoxide; heating to a predetermined first temperature for a predetermined first time; heating to a predetermined second temperature that is higher than the predetermined first temperature for a predetermined second time; cooling the reaction product; and collecting a product.

Figure 8:
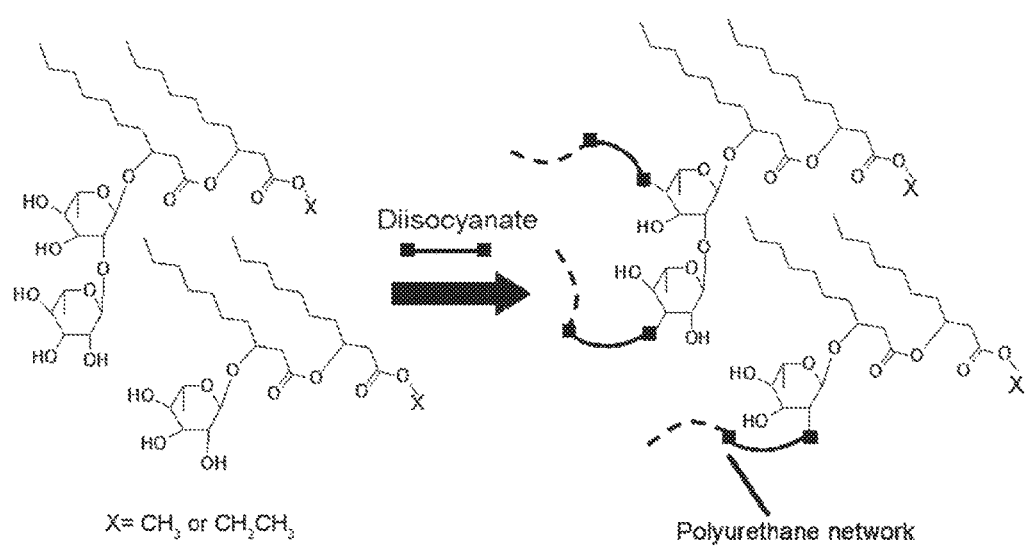
FIG. 8 is a schematic showing the formation of rhamnolipid-based polyurethanes.

The modified rhamnolipids from above having one or more chemical attachments can also be used as monomers or co-monomers to produce polymers or copolymers. Modified rhamnolipids can be selected from the group consisting of methyl rhamnolipids and ethyl rhamnolipids. These polymers can therefore have adjustable properties based on the one or more attachments to the modified rhamnolipids. The modified rhamnolipids have multiple hydroxyl groups, which can then be used for the polymerization such as the polyurethane process shown in FIG. 8. For producing polyurethanes, by reacting with diisocyanates, the rhamnolipids can be cross-linked into polyurethane networks, as shown in FIG. 8. Essentially any diisocyanate can be used and exemplary diisocyanates include toluene diisocyanate, hexane diisocyanate, methylene diphenyl diisocyanate, and combinations thereof.

These formed polymers can have backbones of rhamnose, and one or more attachments if present, and side chains of the one or two β-hydroxy fatty acid residues. Formed polymer can also have side chains of one or two alkyl and/or alkenyl chains. These polymers are environment-friendly, biodegradable, more biocompatible, and can have other improved properties.

One or more methods of polymerization using modified rhamnolipids can include one or more of the following steps: providing rhamnolipids, where the rhamnolipids can be ethylated rhamnolipids, methylated rhamnolipids, or a combination thereof; combining rhamnolipids with a diisocyanate, where the diisocyanate can be 1,6-hexane diisocyanate; adding modified rhamnolipids, where the modified rhamnolipids can be benzene-attached rhamnolipids; curing the combined mixture to produce a polyurethane network; and collecting a product.

EXAMPLES

Example 1: Production of Dimeric β-Hydroxy Fatty Acids from Mono-Rhamnolipids Two grams mono-rhamnolipids, 4 mL sulfuric acid (98%), and 100 mL ethanol were charged in a 500 mL reactor. The reactor was magnetically stirred at 300 rpm and 0° C. The reaction was allowed for 24 h. The sulfuric acid was then neutralized with sodium methoxide (30% in methanol). The salt was removed by centrifugation. The supernatant collected was dried under filtered airflow to remove ethanol and methanol. The precipitate was re-dissolved in toluene to further remove the salt left from centrifuging. The toluene was removed by airflow. Mono-rhamnolipid ethyl esters were obtained as a light yellow product.

Next, 1 g ethylated mono-rhamnolipids was mixed with 25 mL ethanol and 15 mL water. Then 10 mL aqueous sodium hydroxide solution (1% w/w) was added. The reaction mixture was stirred at 300 rpm and 25° C. for 4 h. The sodium hydroxide was neutralized with hydrochloric acid. The reaction mixture was dried with airflow. The precipitate was further purified with silica chromatography, and free dimeric β-hydroxy fatty acids were obtained.

Example 2: Production of Dimeric β-Hydroxy Fatty Acids with a Rhamnolipid Mixture Containing 40% Mono-Rhamnolipids and 60% Di-Rhamnolipids Two grams of a rhamnolipid mixture containing 40% mono-rhamnolipids and 60% di-rhamnolipids, 4 mL sulfuric acid (98%), and 100 mL methanol were charged in a 500 mL reactor. The reactor was magnetically stirred at 300 rpm and 0° C. The reaction was allowed for 24 h. The sulfuric acid was neutralized with sodium methoxide (30% in methanol). The salt was removed by centrifugation. The supernatant collected was dried under filtered airflow to remove methanol by evaporation. The precipitate was re-dissolved with toluene to further remove the salt left from centrifuging. The toluene was removed by airflow. Rhamnolipid methyl esters were obtained as a light yellow product.

Figure 9:
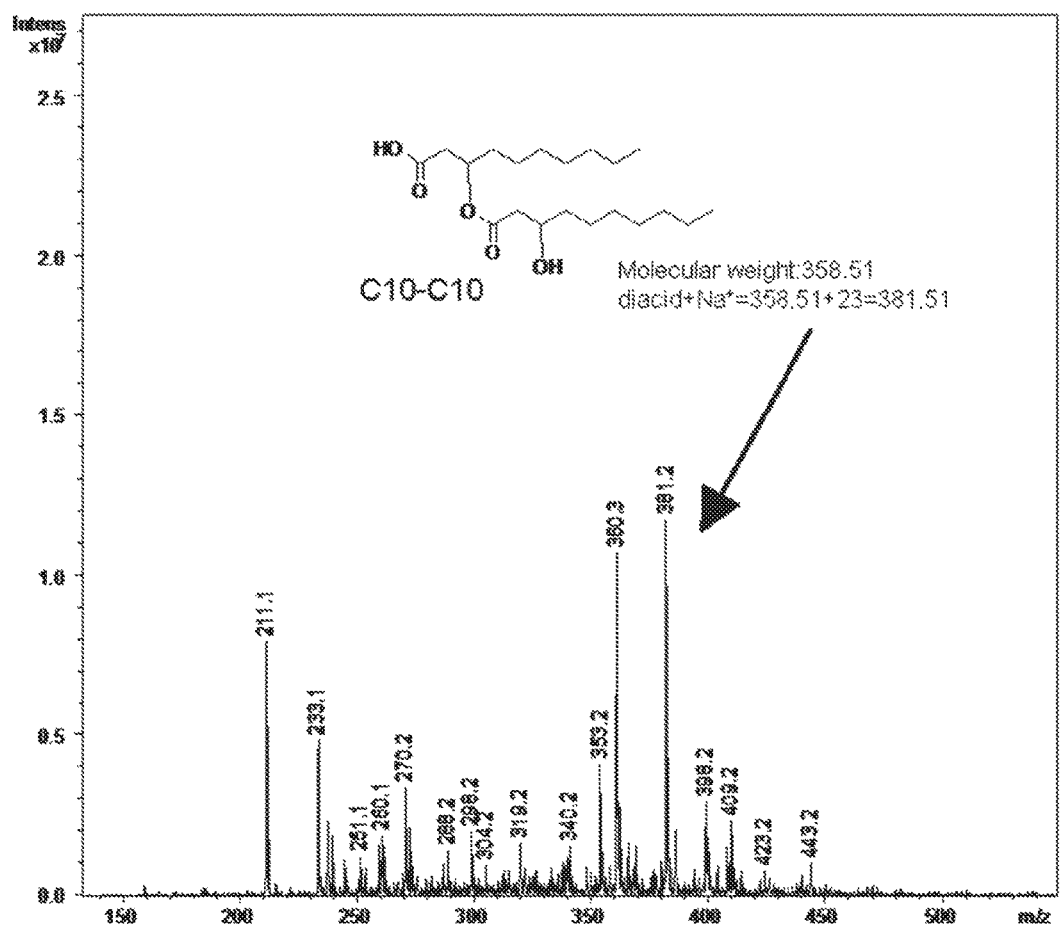
FIG. 9 is a graph showing spectrum results using electrospray ionization mass spectrometer (ESI-MS) under positive mode of particular free dimeric β-hydroxy fatty acids.

One gram methylated rhamnolipids was mixed with 25 mL ethanol and 15 mL water. Then 10 mL sodium hydroxide aqueous solution (1% w/w) was added. The reaction mixture was stirred at 300 rpm and 25° C. for 4 h. The sodium hydroxide was neutralized with hydrochloric acid. The reaction mixture was dried with airflow. The precipitate was further purified with silica chromatography. Free dimeric β-hydroxy fatty acid was obtained, and was characterized with mass analysis, the results of which are shown in FIG. 9.

Figure 10:
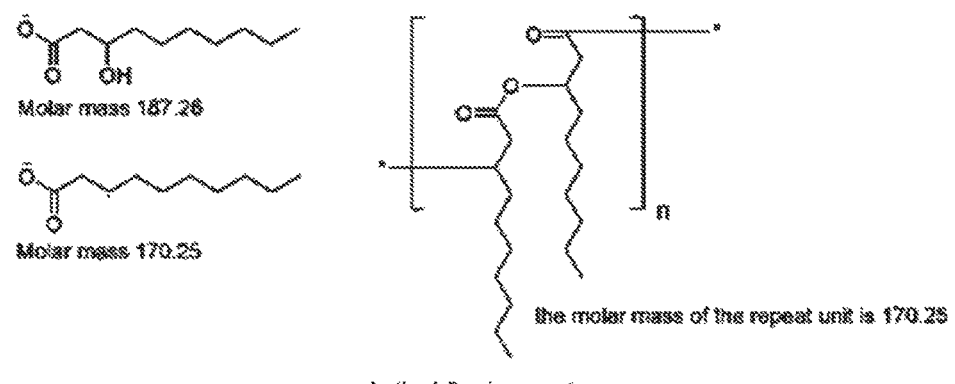
FIG. 10 is a graph showing spectrum results using ESI-MS under negative mode of particular oligomers made from dimeric β-hydroxy fatty acids.
Figure 10:
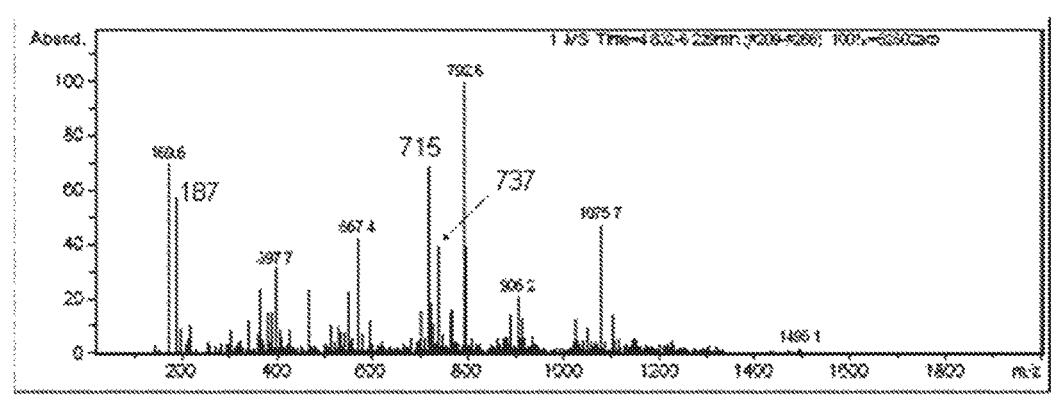

Example 3: Oligomerization of Dimeric β-Hydroxy Fatty Acids 400 mg of dimeric β-hydroxy fatty acids were added to a glass tube. The tube was purged with nitrogen for 30 min. Then the tube was heated to 180° C. and kept at this temperature for 2 h. The temperature was then increased to 210° C. and kept for 2 h. The sample was dissolved in methanol and characterized with high performance liquid chromatography—mass spectrometry (HPLC-MS). These results are shown in FIG. 10.

Example 4: Polymerization of Dimeric β-Hydroxy Fatty Acids 2 g dimeric β-hydroxy fatty acids were added to a glass tube. 10 mg titanium(IV) butoxide was added. The tube was purged with nitrogen for 30 min. Then the tube was heated to 200° C. and kept at this temperature for 2 h. The temperature was then increased to 220° C. and kept for 2 h. A viscous polymer product was obtained after cooling to room temperature under nitrogen gas.

Example 5: Production of Di-Rhamnolipids with One β-Hydroxy Fatty Acid (R—R—$C_n$) from the Common Di-Rhamnolipids with a Chain of Two β-Hydroxy Fatty Acids (R—R—$C_n$—$C_m$)

Figure 11:
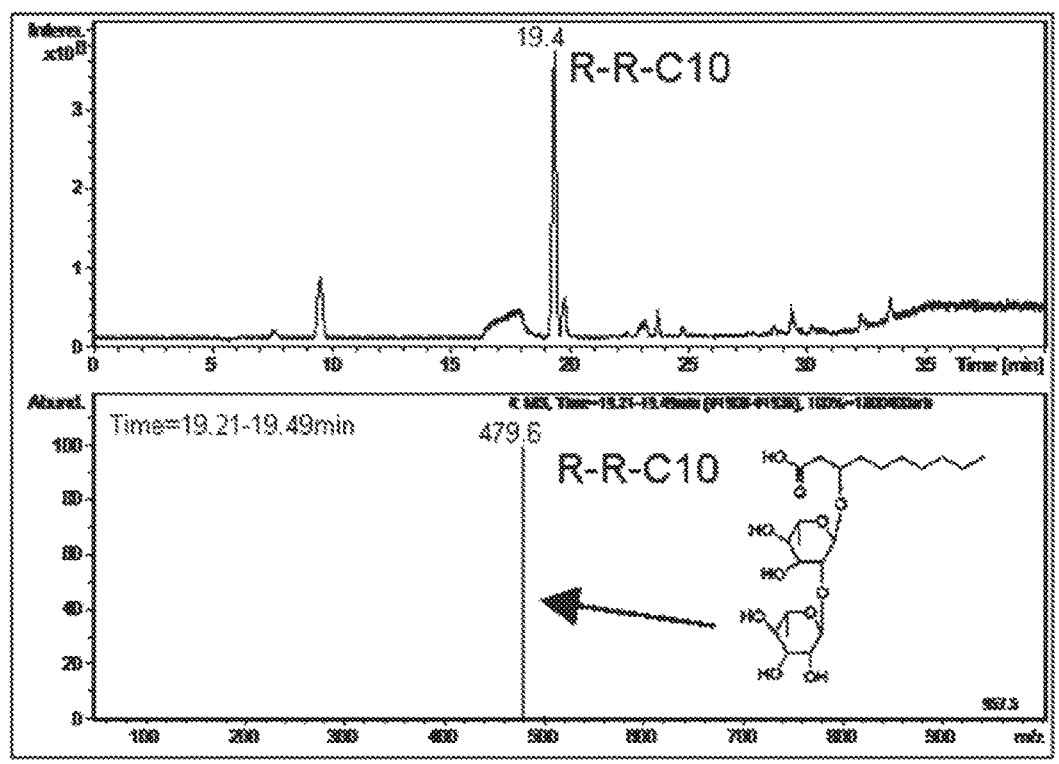
FIG. 11 is a graph showing spectrum results using ESI-MS under negative mode of R—R—$C_{10}$ obtained from the conversion of R—R—$C_{10}$—$C_{10}$.

One gram di-rhamnolipids was mixed with 25 mL water. Two grams sodium hydroxide (98%) was dissolved in 25 mL water. The sodium hydroxide solution was added to the di-rhamnolipid solution. The mixture was stirred at 600 rpm and 50° C. for 4 h. The sodium hydroxide was neutralized with hydrochloric acid. The product was analyzed with HPLC-MS. The results are shown in FIG. 11, which shows that the major product obtained was R—R—$C_{10}$.

Example 6: Production of Mono-Rhamnolipids with One β-Hydroxy Fatty Acid (R—$C_n$) from the Common Mono-Rhamnolipids with a Chain of Two β-Hydroxy Fatty Acids (R—$C_n$—$C_m$)

One gram mono-rhamnolipids was mixed with 50 mL methanol. One mL sodium methoxide (30% w/w in methanol) was added. The mixture was stirred at 600 rpm and 25° C. The reaction was allowed for 6 h. The sodium methoxide was neutralized with hydrochloric acid. The salt was removed by centrifugation. The methanol was removed by airflow, and R—$C_{10}$ was found as the dominant product.

Example 7: Enzymatic Conversion of R—R—$C_n$—$C_m$ to R—$C_n$—$C_m$

Figure 12:
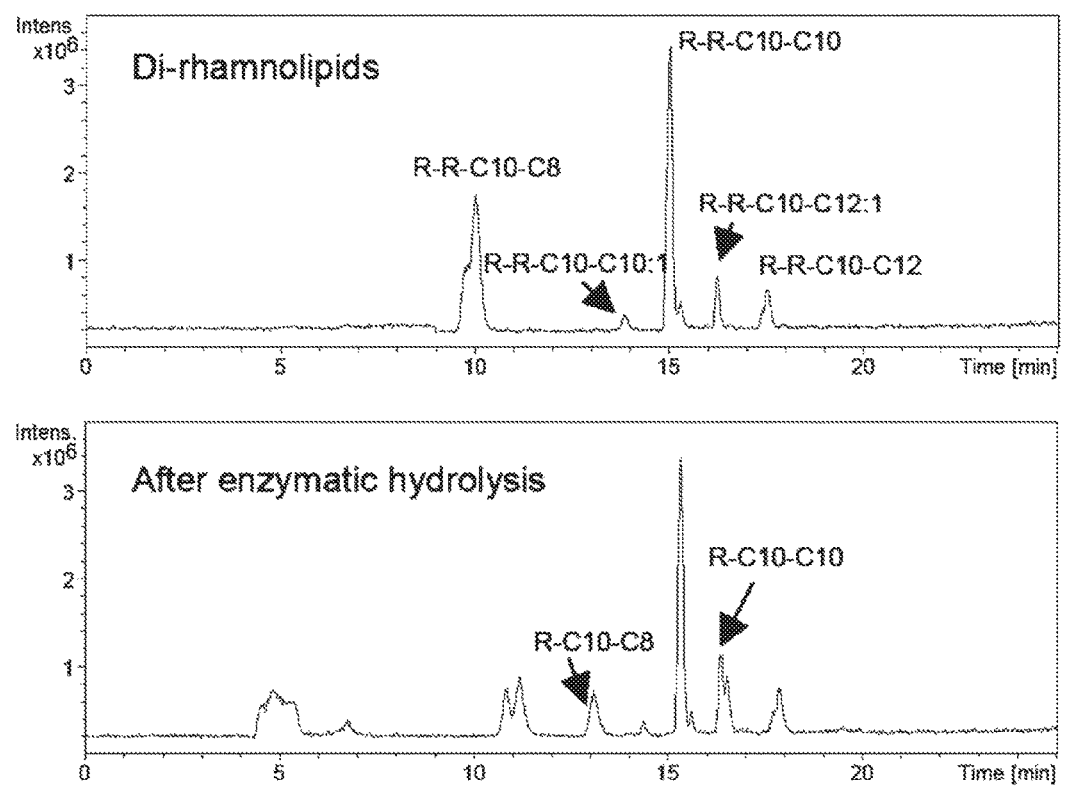
FIG. 12 is a graph showing total ion spectra of a particular rhamnolipid mixture before and after the treatment of being catalyzed by cellobiase, where the changes after treatment indicate the enzymatic conversion of certain di-rhamnolipids to the corresponding mono-rhamnolipids.

Five milligram di-rhamnolipids were dissolved in 5 mL water. Fifty microliter cellobiase solution from *Aspergillus niger* was added to 5 mL 0.05 M citrate buffer at pH 4.8. The enzyme solution was added to the di-rhamnolipid solution. The mixture was shaken at 300 rpm and 37° C. for 24 h. The enzymatic conversion was monitored with HPLC-MS, with the results provided in FIG. 12. As shown in FIG. 12, about 20% di-rhamnolipids were converted to mono-rhamnolipids after 24 h.

Based on the product peaks formed, R—R—$C_{10}$—$C_8$ and R—R—$C_{10}$—$C_{10}$ were hydrolyzed by the cellobiase to their corresponding mono-rhamnolipid counterparts, while no conversion was detected for R—R—$C_{10}$—$C_{12:1}$ and R—R—$C_{10}$—$C_{12}$. Without being limited to any theory, it is possible that the enzymatic conversion is related to the fatty acid chain length. R—R—$C_{10}$—$C_8$ has the shortest chain length and was hydrolyzed the most. R—R—$C_{10}$—$C_{10}$ was also hydrolyzed. The longer fatty acid chains in R—R—$C_{10}$—$C_{12:1}$ and R—R—$C_{10}$—$C_{12}$ might have affected the affinity of these rhamnolipids for the active site of the enzyme.

Example 8: Enzymatic Conversion of R—R—$C_n$—$C_m$ to R—$C_n$—$C_m$ with a Rhamnolipid Mixture Initially Containing about 40% Mono-Rhamnolipids and 60% Di-Rhamnolipids Five milligram of a rhamnolipid mixture of about 40% mono-rhamnolipids and about 60% di-rhamnolipids was dissolved in 5 mL water. Fifty microliter cellobiase solution from *Aspergillus niger* was added to 5 mL 0.05 M pH 4.8 citrate buffer. The enzyme solution was added to the rhamnolipid solution. The mixture was shaken at 300 rpm and 37° C. for two days. The content of di-rhamnolipids in the rhamnolipid mixture decreased from about 60% to about 45%, and the content of mono-rhamnolipids in the rhamnolipid mixture increased from about 40% to 55%.

Figure 13:
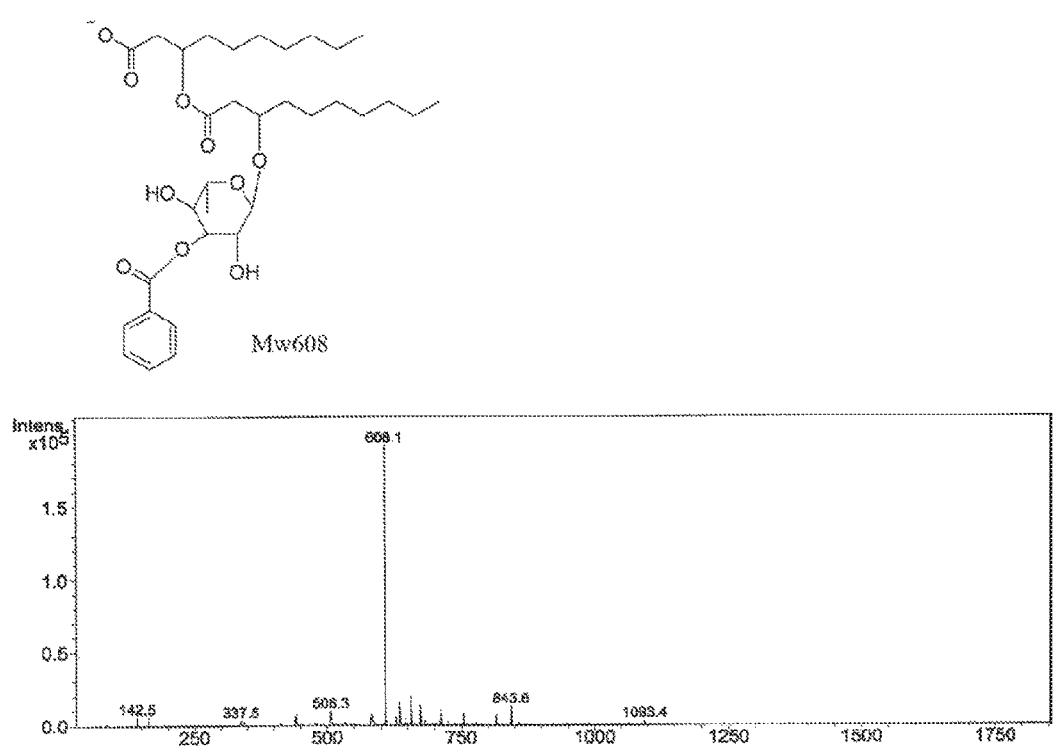
FIG. 13 is a graph showing spectrum results using ESI-MS under negative mode of the product of the schematic from FIG. 5.

Example 9: Modification of Rhamnolipids with Benzoyl Chloride 50 mg of rhamnolipids were charged in a 2 mL glass vial. 0.5 mL of benzoyl chloride was added. The vial was put into a 30° C. shaker operating at a shaking speed of 180 rpm. 0.2 mL of acetonitrile was mixed with 0.02 mL triethylamine and the mixture was added into the rhamnolipid mixture slowly, drop by drop with each drop of about 0.05 mL. The reaction was allowed for 24 h, and the product was analyzed with mass spectrometry. The results are shown in FIG. 13.

Example 10: Modification of Rhamnolipids with Acetylated Glucose

Figure 14:
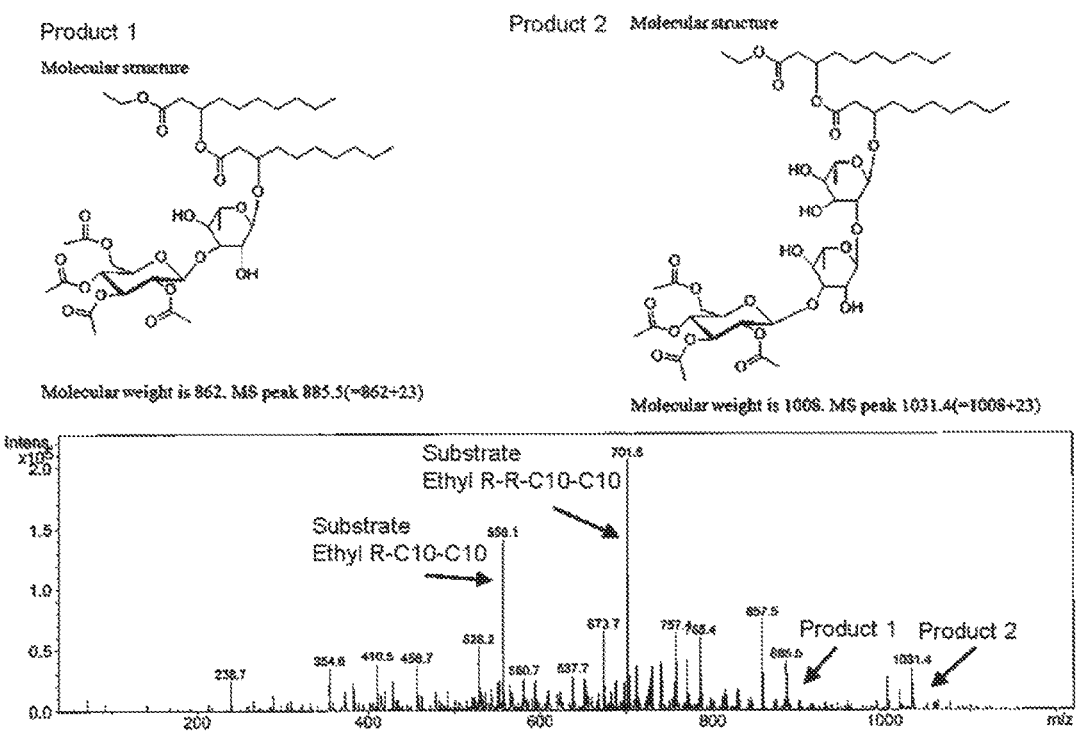
FIG. 14 is a graph showing spectrum results using ESI-MS under positive mode of the product of the schematic from FIG. 7.

Ethylated rhamnolipids were first produced according to the method described as part of Example 1. 90 mg of the ethylated rhamnolipids were charged in a glass vial. One milliliter of a 2,3,4,6-tetra-β-D-glucopyranosyl bromide solution was added. Then 80 mg 1,1,3,3-tetramethylurea and 120 mg silver carbonate were added. The glass vial was wrapped with a black plastic sheet to avoid penetration of ambient light. The reaction was allowed for 3.5 h at 25° C. The products were analyzed with mass spectrometry (FIG. 14).

Example 11: Preparation of Polyurethanes from Ethylated Rhamnolipids

Figure 15:
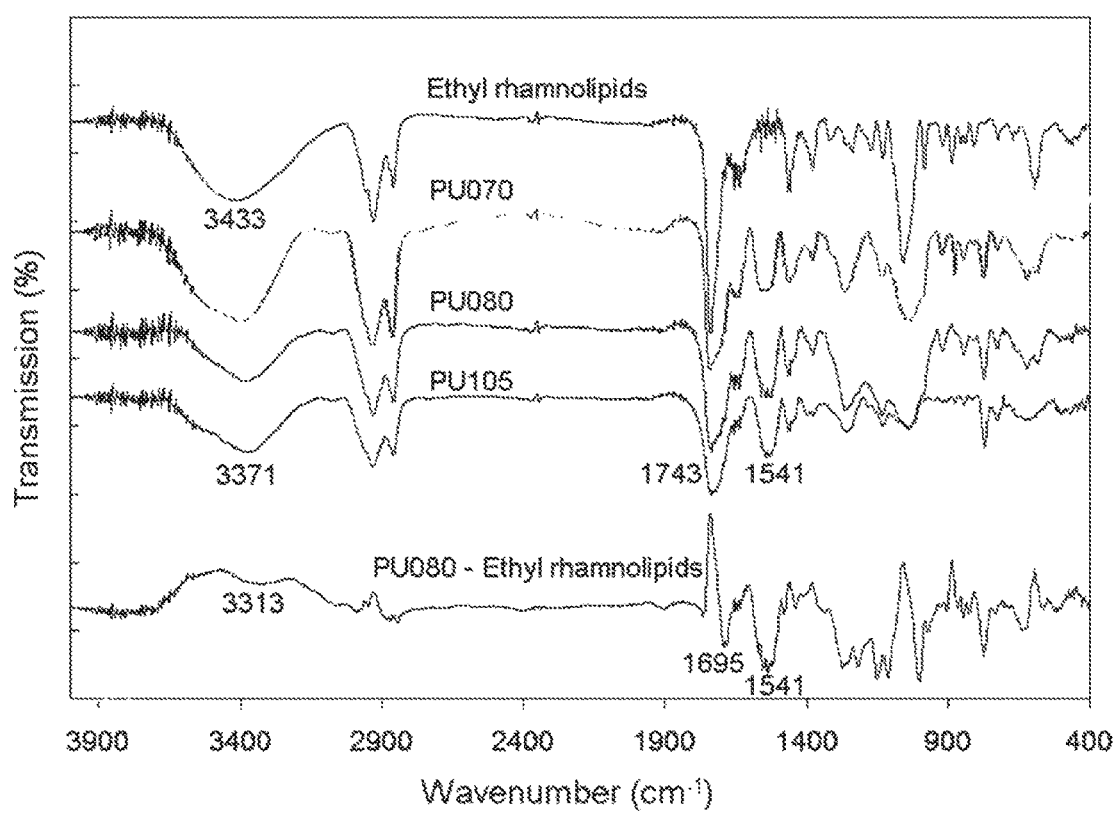
FIG. 15 is a graph showing results from Fourier transform infrared spectroscopy (FTIR) analysis of particular rhamnolipids-based polyurethanes.

One gram ethylated rhamnolipids was put in each of three 25 mL glass vials. An amount of 1,6-hexane diisocyanate was added to each vial. The amounts added were 0.85 g, 0.97 g, and 1.23 g. Reactants were mixed homogenously and centrifuged for 5 min at 4000 g to remove bubbles. Then, the vials were put in an oven for two 24-h curing steps: first at 80° C. and then at 100° C. The molar ratio of isocyanate groups to hydroxyl groups was set at 0.70:1, 0.80:1 and 1.05:1, respectively, and the corresponding polyurethane samples were coded as PU070, PU080, and PU105 in FIG. 15. The Fourier transform infrared spectroscopy (FTIR) analysis results are shown in FIG. 15.

The signal at 1541 $cm^{-1}$ corresponds to the N—H deformation in a urethane bond, indicating the polyurethane formation. The signal for C=O vibration in the urethane bond, at 1695 $cm^{-1}$, is a shoulder overlapping with the signal for ester group at 1745 $cm^{-1}$, but it can be clearly seen after, e.g., the spectrum of PU080 is corrected for the ethyl rhamnolipid structure. The signal at 3371 $cm^{-1}$, corresponding to stretching vibration of N—H, further confirms the formation of polyurethane.

Example 12: Preparation of Polyurethane Containing Modified Rhamnolipids

One gram ethylated rhamnolipids was put in a 25 mL glass vial. 1.5 grams of 1,6-hexane diisocyanate were added. 0.5 g of benzene-attached rhamnolipids, prepared as described in Example 9, were added. The reactants were mixed homogenously and centrifuged for 5 min at 4000 g to remove bubbles. Then, the vial was put in an oven for two 24-h curing steps: first at 80° C. and then at 100° C. to produce the polyurethane containing both ethylated rhamnolipids and benzene group-modified rhamnolipids in the cross-linked network.

Various modifications and alterations that do not depart from the scope and spirit of this invention will become apparent to those skilled in the art. This invention is not to be duly limited to the illustrative embodiments set forth herein.

What is claimed is:

1. A method of preparing a product derived from a rhamnolipid comprising steps of:
   providing a rhamnolipid;
   combining the rhamnolipid with a reagent;
   allowing the rhamnolipid and the reagent to react to form a product derived from the rhamnolipid, where the step of allowing does not utilize an enzyme;
   collecting the product derived from the rhamnolipid, where the product derived from the rhamnolipid is a compound having the following formula:

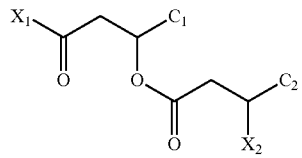

where $C_1$ and $C_2$ are each a hydrocarbon chain having between four and fourteen carbon atoms, and where $X_1$ and $X_2$ are each selected from the group consisting of a hydroxyl group and an alkoxy group, and
   polymerizing the product derived from the rhamnolipid.

2. The method of claim 1, where $C_1$ and $C_2$ are each alkyl chains having seven carbon atoms.

3. The method of claim 2, where $X_1$ and $X_2$ are each hydroxyl groups.

4. A method of modifying a rhamnolipid comprising the steps of: providing a rhamnolipid having the following formula:

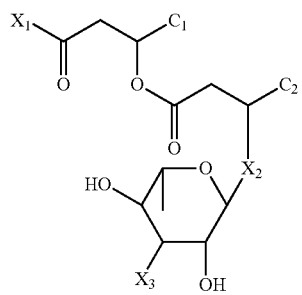

where $C_1$ and $C_2$ are each a hydrocarbon chain having between four and fourteen carbon atoms, where $X_1$ is selected from the group consisting of a hydroxyl group and an alkoxy group, where $X_2$ is oxygen; and chemically attaching a compound at position $X_3$, where the chemically attached compound is selected from the group consisting of

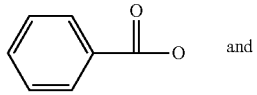 and 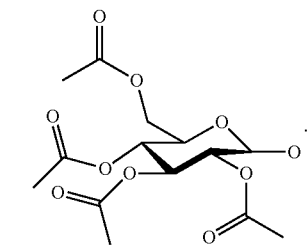

5. The method of claim 4, where $C_1$ and $C_2$ are each alkyl chains having seven carbon atoms.

6. The method of claim 4 where the chemically attached compound is

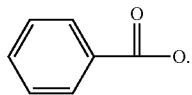

7. The method of claim 4 where the chemically attached compound is

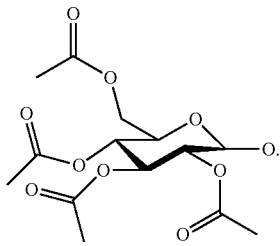

8. The method of claim 7, further comprising the step of polymerizing the modified rhamnolipid.

9. The method of claim 7, further comprising the step of polymerizing the modified rhamnolipid.

10. A method of preparing a product derived from a rhamnolipid comprising steps of:
    providing a rhamnolipid,
    combining the rhamnolipid with a reagent, where the reagent is selected from the group consisting of benzoyl chloride and acetylated glucose,
    allowing the rhamnolipid and the reagent to react to form a product derived from the rhamnolipid, and
    collecting the product derived from the rhamnolipid.

11. The method of claim 10, wherein the reagent is benzoyl chloride.

12. The method of claim 10, wherein the reagent is acetylated glucose.

13. A method of preparing a product derived from a rhamnolipid comprising steps of:
    providing a rhamnolipid,
    combining the rhamnolipid with an acid,
    allowing the rhamnolipid and the acid to react in the presence of an alcohol, to form a product derived from the rhamnolipid, wherein the step of allowing does not utilize an enzyme, wherein the rhamnolipid is provided by a rhamnolipid mixture comprising both mono-rhamnolipids and di-rhamnolipids, and wherein the product derived from the rhamnolipid is dimeric β-hydroxy fatty acid,
    combining a catalyst with the dimeric β-hydroxy fatty acid to form a catalyst and product mixture, and
    heating the catalyst and product mixture,
    whereby the steps of combining and heating polymerize the dimeric β-hydroxy fatty acid.

14. A method of preparing a product derived from a rhamnolipid comprising steps of:
    providing a rhamnolipid,
    combining the rhamnolipid with a reagent, wherein the reagent is a diisocyanate,
    allowing the rhamnolipid and the reagent to react to form a product derived from the rhamnolipid, and
    collecting the product derived from the rhamnolipid, wherein the product derived from the rhamnolipid is a polyurethane.

15. The method of claim 14, where the rhamnolipid is a mono-rhamnolipid ethyl ester.

16. The method of claim 14, the rhamnolipid having the formula

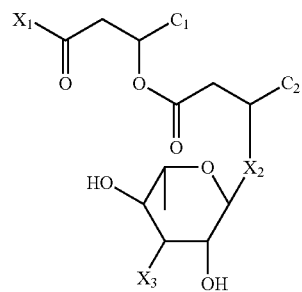

wherein $C_1$ and $C_2$ are each a hydrocarbon chain having between four and fourteen carbon atoms, wherein $X_1$ is selected from the group consisting of a hydroxyl group and an alkoxy group, where $X_2$ is oxygen, wherein $X_3$ is selected from the group consisting of

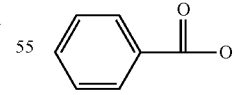 and 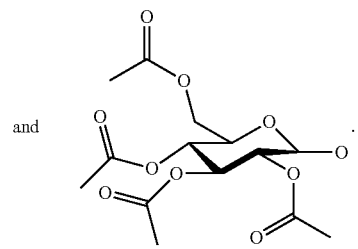

* * * * *